United States Patent [19]
Parisi

[11] Patent Number: 4,816,018
[45] Date of Patent: Mar. 28, 1989

[54] ULTRASONIC PROBE TIP

[75] Inventor: Tulio Parisi, San Diego, Calif.

[73] Assignee: Ultramed Corporation, San Diego, Calif.

[21] Appl. No.: 62,243

[22] Filed: Jun. 15, 1987

Related U.S. Application Data

[63] Continuation of Ser. No. 762,548, Aug. 2, 1985, abandoned.

[51] Int. Cl.⁴ .............................................. A61B 17/20
[52] U.S. Cl. ..................................... 604/22; 128/24 A
[58] Field of Search ....................... 604/27, 28, 31, 51, 604/73, 247

[56] References Cited

U.S. PATENT DOCUMENTS

| | | | |
|---|---|---|---|
| 4,098,275 | 7/1978 | Consalvo | 604/22 X |
| 4,428,748 | 1/1984 | Peyman et al. | 604/22 |
| 4,504,264 | 3/1985 | Kelman | 604/28 X |
| 4,513,745 | 4/1985 | Amoiks | 604/22 X |
| 4,516,398 | 5/1985 | Wuchinich | 604/35 X |
| 4,531,934 | 7/1985 | Kossovsky et al. | 604/35 X |

OTHER PUBLICATIONS

Wells, P.N.T. "Biomedical Ultrasound", (textbook), pp. 58-60, 1977, Academic Press, N.Y., (copy AU335).

Primary Examiner—Francis J. Jaworski
Attorney, Agent, or Firm—Ellsworth R. Roston; Charles H. Schwartz

[57] ABSTRACT

An ultrasonic probe tip is provided with improved characteristics for removing material during surgery on a cataract or the like, and reducing the removed material into smaller particles. The tip includes a body section and a cutting section with a passage extending through both sections. Aspiration is provided to the passage means through a collector passageway within a smooth, cylindrical head. An annular sharpened edge on the cutting section removes the material and emulsifies the particles. The cutting section is an enlarged chamber to receive a core stream of liquid from the operation site drawn into and defined by the smaller passage in the body section to generate vortex action clearing the operation site, reducing the size of the particles to prevent clogging and prevent cavitation. The interior surface of the enlarged chamber can be roughened, such as by etching, in order to provide additional emulsification action. The tip is fabricated of titanium and used on conventional ultrasonic handpieces.

21 Claims, 1 Drawing Sheet

ULTRASONIC PROBE TIP

This is a continuation of application Ser. No. 762,548, filed Aug. 2, 1985 now abandoned.

BACKGROUND OF THE INVENTION

The present invention pertains generally to ultrasonic probes and, more particularly, to an improved ultrasonic probe tip which emulsified and more efficiently removes tissue as it is aspirated through the tip.

Until the late 1960's, ophthalmological surgical techiques for cataract removal were performed using standard intracapsular cataract extraction techniques which, although generally satisfactory, require a prolonged recovery time of up to several months. Since that time, a procedure known as phacoemulsification, or use of an ultrasonic probe to break up and remove cataracts, has become widely used because it offers a remarkable decrease in recovery time. Indeed, a patient can sometimes return to work the day after surgery with this new technique.

The procedure for removal of cataract tissue is described in the article entitled "History of Emulsification and Aspiration of Senile Cataracts," by Charles D. Kelman, appearing in Transactions American Academy of Ophthalmology and Otolaryngology, Volume 78, January-February, 1974, pp. OP5-13 (originally presented at the 78th Annual Meeting of the American Academy of Ophthalmology and Otolaryngology, Dallas, Tex., Sept. 16-20, 1973). Generally speaking, a tip in the form of a hollow tube is inserted into the anterior chamber of the eye through a small incision into contact with the cataract tissue. The tip is vibrated by a hand held probe at an ultrasonic rate, and hydrodynamic flow of a saline solution is establisohed in order to prevent collapse of the anterior chamber. As particles of the cataract tissue are cut from the cataract mass, the particles are removed from the chamber through the tip of the ultrasonic probe. In the case of hard cataracts, these particles, which have a tendency to slide into contact with the walls of the chamber, have an abrasive character. Since certain portions of the eye including the chamber walls are very prone to abrasion sensitivity, the cataract particles must be quickly, and as completely as possible, removed from the chamber. This is done by aspiration through the hollow tip.

During aspiration of cataract tissue, the tip of the ultrasonic probe must be very carefully manipulated under the field of view of a microscope in order to prevent aspirating other than cataract tissue and to insure that all the cataract particles are removed from the chamber. Close control of the tip is especially critical at the peripheral regions of the cataract. The tip must be able to efficiently remove the cataract tissue without clogging or otherwise hindering the surgical procedure.

Several improved ultrasonic probes have been developed for performing this and other delicate types of surgery as well as cleaning of teeth and the like. These probes generally also consist of a tip for cutting/cleaning material at the operation site, a hand piece for mounting the tip and associated circuitry, and a pieoelectric crystal or other means for supplying ultrasonic energy to vibrate the tip. My prior design disclosed in U.S. Pat. No. 4,169,984, is one of the most innovative, greatly improving the ultrasonic handpiece capable of use with a variety of tips for removing cataract tissue, cleaning and similar functions. While remarkable advances have thus been made in the total instrument and the technique of use, the basic design of the tips has remained unchanged over the years. U.S. Pat. No. 4,428,748 to Peyman et al., issued in 1984, is typical of the attempts that have been made to modify the probe tip. In this instance an additional drive mechanism is required in an attempt to provided better cutting action. However, even with this expensive modification, such designs, like other prior art inventions that I am aware of, are hampered by slow cutting action, clogging and generally unsatisfactory performance.

To put it another way, prior ultrasonic probe tips have not proved to be as effective and efficient in removing the undesired tissue as they could be. The cutting edge of the probe tip often shears large pieces of cataract tissue which cannot easily be aspirated with the smal diameter tip. These particles tend to either not be aspirated and, therefore, left in the eye to damage walls of the eye, or, as is often the case, clog the tip and prevent aspiration of the particles. If the tip clogs, surgery must be halted to clean or change the tip. The delay in surgery increases the trauma and risk to the patient. A new and improved ultrasonic probe tip which can efficiently remove severed tissue, emulsify the tissue into fine particles and avoid the surgical delays caused by tip clogging is, therefore, needed.

Accordingly, one object of the invention is to provide a new and improved probe tip for ultrasonically removing tissue.

A further object of the present invention is to provide a new and improved ultrasonic probe tip which will not clog during the surgical procedure.

Another object of the invention is to provide a new and improved ultrasonic probe tip for performing phacoemulsification for cataract removal.

Still another object of the invention is to provide a new improved and low cost probe tip and method for performing cataract particles are phacoemulsification wherein cataract particles are efficiently aspirated from the anterior chamber to avoid damage to delicate eye tissue.

BRIEF DESCRIPTION OF THE INVENTION

An ultrasonic probe tip for removing tissue from a surgical site, particularly for removing cataract tissue from within the eye, comprises a hollow needle-like tube having a sharp annular end for cutting away the undesirable tissue and a hollow inner passage for aspiration of the removed tissue. The inner passage has at least two different diameters along the tip; the distal or cutting section of the tip having a larger inner passage diameter than the body section. The passage in the distal section, therefore, forms an enlarged chamber having a relatively thin wall while the body section forms a smaller passage having a relatively thick wall. The larger chamber in the distal section is formed by reducing the thickness of the tip wall from the interior. The outer diameter of the tip remains constant for the length of the tip to provide optimum ultrasonic vibratory action.

As the tissue particles are severed from the cataract or other unwanted growth, the sharp annular end is more effective in chopping the particles into fine pieces. The boundary layer of the aspirated core stream defined by the reduced inner passage in the body section of the tip, sets up an exterior vortex ring around the end of the tip clearing the operation site and causing the particles to repeatedly come in contact with the sharp edge.

As these reduced particles are aspirated through the tip, additional vortex action generated by the stream and the difference in diameter of the inner passage causes the tissue particles to be further emulsified. Cavitation is advantageously prevented by the boundary layer pumping effect as liquid from the surrounding operation site is pulled into the chamber.

Preferably, the inner surface of the enlarged chamber is roughened, such as by chemical etching. The particles are stirred and caused to impact the roughened interior of the chamber many times. Multiple impacts with the rough surface emulsify the large tissue particles, breaking them into many small particles, and making aspiration of the particles easier. The tip, thereafter, ca be used for prolonged periods without clogging caused by the large tissue particles. Delays in surgery and the resulting trauma to the patent caused by clogging in prior art tips are greatly reduced or eliminated.

Other objects, advantages, and novel features of the present invention will become apparent from the following detailed description of the invention.

BRIEF DESCRIPTION OF THE DRAWINGS

FIG. 3 is an enlarged cross-sectional view of the cutting end ofthe tip showing the actual cutting and emulsification action that takes place on a cataract or the like.

DETAILED DESCRIPTION OF THE PREFERRED EMBODIMENT

Figure 1:
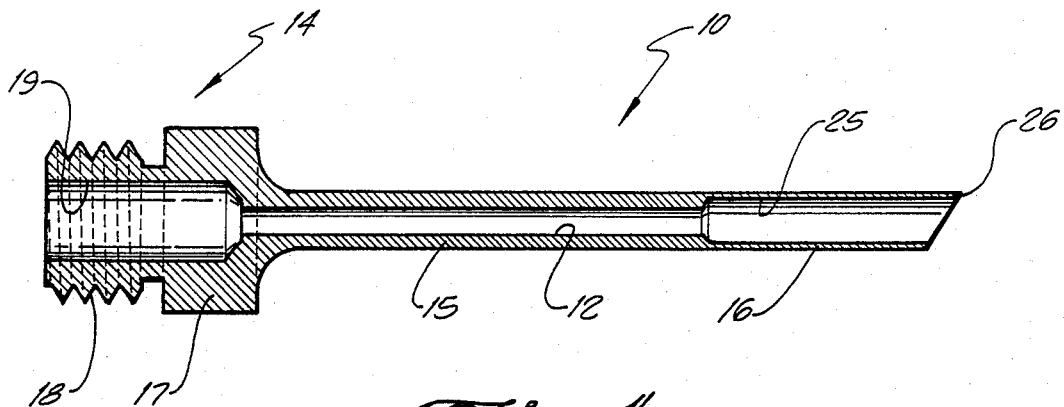
FIG. 1 is a side cross-sectional view of an ultrasonic probe tip showing the configuration of the tip of the present invention illustrating the structural features that allow more efficient tissue removal and emulsification.

Referring to FIG. 1, an elongated ultrasonic probe tip 10, used for ultrasonically removing cataract tissue or other unwanted material is shown in its preferred form. Within the tip 10 is an inner passage 12 running the full length as shown in the drawings. The tip is divided into three sections, a head section 14, a body section 15 and a distal or cutting section 16. The head section 14 includes a cylindrical flange 17 and a threaded connector 18. Inside the head 14 is an aspiration collector passageway 19.

Figure 2:
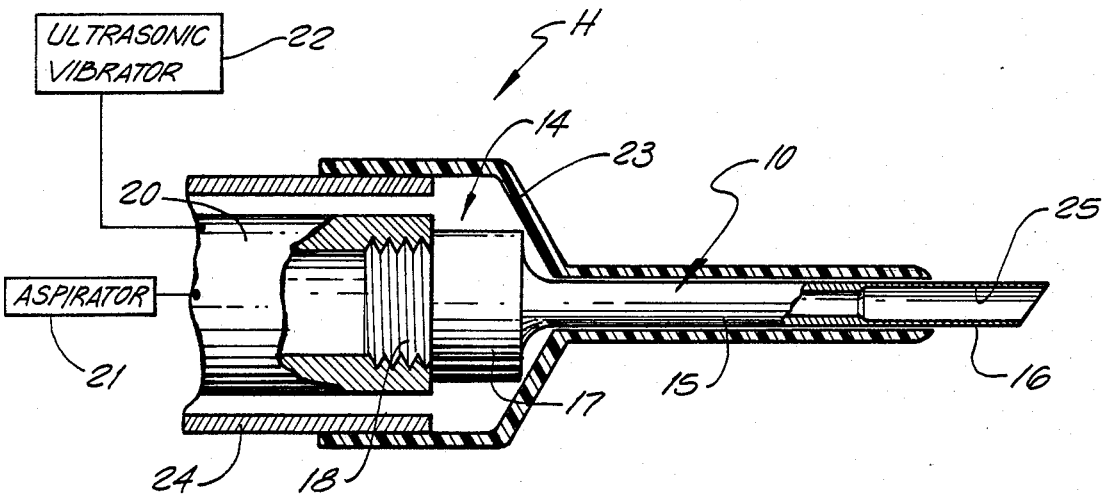
FIG. 2 is a cross-sectional view of the tip mounted on an ultrasonic generator handpiece for use.

As best shown in FIG. 2, the head section 14 of the tip 10 is designed to be attached to a complete ultrasonic handpiece H. Thus, the tip 10 is supported on an ultrasonic driver 20 having a hollow interior and connected to a suitable aspirator 21 and ultrasonic vibrator 22. As is known in the art, the aspirator 21 is connected to the collector passageway 19 to form the aspiration means for the tip 10 after being connected by the threaded portion 18. As shown, the sections 15, 16 have a constant outside diameter to provide a smooth tubular surface and the flange 17 is also perfectly smooth, that is cylindrical without any raised edges. This enhances the ultransonic vibratory action from the driver 20 so that the maximum cutting action is transmitted to the tip 10.

When a surgeon is ready to use the tip 10 of the present invention, assuming that removable skirt 23 is detached from housing 24 of the handpiece H, the head section 14 is threaded into the driver 20 so that it is initially hand tight (see FIG. 2). With a special wrench engaging the flange 17, disclosed and claimed in my copending patent application entitled Wrench Assembly for Securing and Removing a Tip from an Ultrasonic Probe, filed Jan. 13, 1986, Ser. No. 818,013, the tip 10 is firmly tightened. The skirt 23 is placed back in position on the housing 24, the aspirator 21 and the ultrasonic vibrator 22 is turned on. A separate supply of saline solution from a supply tube (not shown) is positioned adjacent the operation site and the operation is ready to begin. In the case of a cataract operation, the cutting section 16 of the tip and the solution supply tube is placed in an incision in the eye and the successful phacoemulsification commences in a manner as will be described in detail below.

Figure 3:
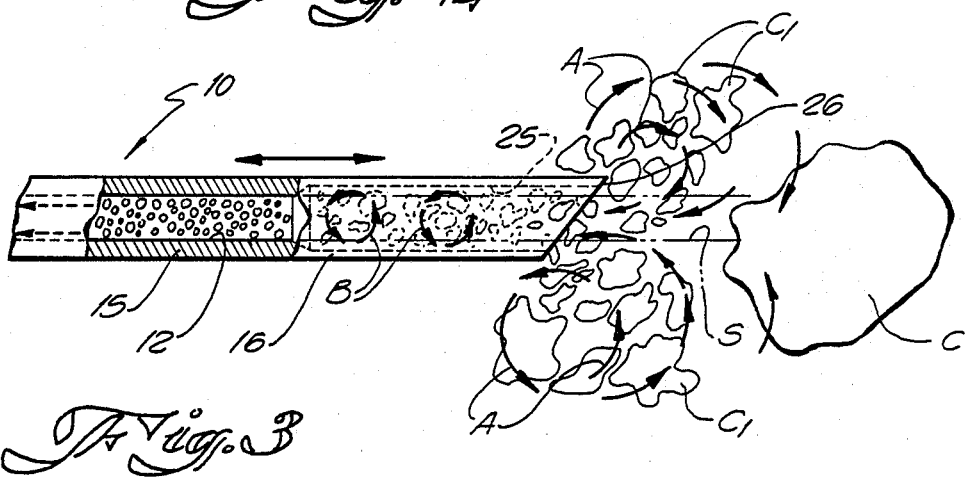

First, with reference to FIGS. 1 and 3 in combination, a more detailed description of the inventive aspects of the tip 10 of the present invention is required. The tip 10, as briefly described above, is a needle-like hollow tube with the body section 15 and the cutting section 16 forming the improvement that provides for the more efficient cutting and emulsification action. Specifically, the passage means 12 includes an enlarged chamber 25 in the cutting secton 16. The chamber 25 is formed by machining a larger inner passage diameter than in the body section 15. The enlarged chamber 25 thus has a relatively thin wall while the passage in the body section 15 is thicker. The thicker body section wall provides the required support along the body section, whereas the thin wall of the cutting section also provides for a thinner and thus sharper annular cutting end 26. The outer diameter of the probe tip 10 remain the same along the entire length from the head 14 to the end 26 providing for the optimum ultrasonic vibratory action.

As is well known, the operation site, such as in a cataract operation, is flooded with liquid solution, preferably a saline solution. This maintains the material being operated on and the particles being removed in suspension thus allowing efficient hydraulic aspiration through the passage 12. The operation site flooded with liquid solution is depicted in FIG. 3 where a cataract C is being operated on with an annular vortex ring being defined by removed particles C1 around the perimeter of the cutting end 26. The showing of FIG. 2 depicts the tip 10 having removed a portion of the cataract C generating the particles C1 and having backed away slightly from the operation site to allow the particles C1 to be broken up, emulsified and aspirated through the passage 12. The skilled surgeon deftly moves the tip 10 toward and away from the operation site alternately cutting away and allowing full aspiration of the particles until the entire mass C is disintegrated.

As the aspiration is established through collector passageway 19 and the passage 12, a core stream S is generated in the operation area, as depicted by the dashed/dot line outline in FIG. 3. As shown, this core stream is generally the size of the reduced inner passage within the body section 15 and is made up of the fastest moving liquid molecules. The core stream starts adjacent the operation site and extends through the enlarged chamber 25.

As the core stream moves through the flooded operation area, the boundary layer tends to entrain the surrounding liquid molecules setting up a desired vortex ring around the annular end 26 (see FIG. 3). This vortex ring is generally depicted by the action arrows A. This vortex ring action, although not understood in its entirely, is believed to perform two important functions that have not been possible with ultrasonic probe tips of the prior art without an enlarged distal chamber; namely, (1) a clearance of the operation site around the cataract C (note space between the particles C1 and the cataract C) and (2) a circulating movement of the particles C1 so as to be brought repeatedly into engagement with the sharpened annular end 26 for splitting, resplitting and emulsification into smaller and smaller particles.

Inside the enlarged chamber 25, additional vortex action is generated by the stream and the difference in diameter of the inner passage. The particles within the chamber are further emulsified as the liquid moleculars stir and agitate the particles breaking them apart. In this regard, note the action arrows B in FIG. 3.

Preferably, in accordance with a more limited aspect of the present invention, the probe tip 10 is fabricated of titanium and the inner surface of the chamber 25 is roughened, such as by etching of the metal surface. This roughening can be by chemical etching using hydrochloric acid, for example, or can be by mechanical scoring of the metal. The multiple impacts of the particles with the roughened interior of the chamber serve to further emulsify the particles breaking them into smaller and smaller particles and making aspiration easier and helping to virtually eliminating clogging of the tip 10.

Another drawback of prior art tips is avoided by the enlarged chamber 25 of the present invention. That is, deleterious cavitation or formation of air pockets around the operation site, at the mouth of the tip and along the passage 12 is avoided. This advantageous action is also attributed to the benefits of the core stream with the boundary layer pumping serving to effectively draw surrounding liquid to the operation site and into the chamber 25. Since the stream S is spaced from the surface of the chamber 25, there is room for the additional liquid to enter and collapse any air pockets that would tend to form along the surface. To put it another way, the space prevents complete evacuation along the surfaces which previously would have led to air pockets, as is well known in the art of fluids and particularly the art of fluidics. Without cavitation, the flow of fluid remains smooth and constant eliminating a significant source of clogging and indeed minimizing trauma to the operation site.

In summary, the probe tip 10 of the present invention having an enlarged distal chamber 25 provides significant results and advantages over the prior art tips. During a phacoemulsification operation or the like, the ultrasonic cutting of the unwanted tissue and the breaking up and emulsification of the particles is substantially enhanced. The core stream S defined by the passage 12 in the body section 15 of the tip 10 provides for a smooth circulating action in a vortex ring around the sharpened annular end 26. The operation site is cleared continually and the particles are caused to have multiple impacts against the end for more efficient splitting and emulsification. The probe tip 10 can therefore access the operation site more easily, do a better job emulsifying the particles and prevent clogging, thus significantly reducing the time required for the surgery. The vortex action within the enlarged chamber 25 and the roughened surface further emulsifies the severed tissue and aids in the removal procedure. The boundary layer effect fills in any voids around the operation site or within the enlarged chamber 25, thus virtually eliminating cavitation and providing for the first time smoother and more efficient liquid flow.

Obviously, many modifications any varations of the present invention are possible in light of the above teachings. It is therefore to be understood that within the scope of the appended claims, the invention may be practiced otherwise than as specifically described.

I claim:

1. An ultrasonic probe tip for removing unwanted material and reducing said material into smaller particles for aspiration comprising;
   a body section and a distal section said body and distal sections being adapted to receive ultrasonic vibratory energy from a source and to convey said vibratory energy to said material disposed in coupled relationship to the body section, the body section being spaced from the distal section in the direction of removal of the unwanted material;
   an annular edge on said distal section to remove the material and reduce such material to smaller particles; and
   passage means extending through said body and distal sections and communicating with the annular edge for the withdrawal of the particles from the tip by aspiration, said passage means having vortex action generating means including a relatively small diameter passage disposed in said body section and an extended and enlarged chamber disposed in said distal section and communicating directly with said relatively small diameter passage in said body section in the direction of movement of the smaller particles of the unwanted material through the passage means; said relatively small diameter passage defining a core stream drawn into and through said extended and enlarged passage in said distal section whereby vortex action is generated in the enlarged chamber by boundary layer effect to clear the unwanted material, assist in reducing the size of the particles to prevent clogging in said passage means and to prevent cavitation.

2. The probe tip of claim 1 wherein the inner surface of said enlarged chamber in said distal section is roughened to further assist in reducing the size of the particles.

3. The probe tip of claim 2 wherein the roughened surface in said enlarged chamber is etched.

4. The probe tip of claim 1 wherein said tip has an annular cross-sectional shape of a substantially constant outer diameter in the body section and in the distal section for optimizing the ultrasonic action.

5. The probe tip of claim 4 wherein said tip includes a head with a smooth cylindrical surface.

6. The probe tip of claim 1 wherein said tip is made from titanium.

7. A method of ultrasonically removing unwanted material and reducing said material into smaller particles comprising the steps of:
   providing a hollow tube including a passage at one end of the tube for particle aspiration and further including an enlargement of the passage at the other end of the tube and further including a sharpened annular edge at the end of the passage for particle aspiration, the passage communicating with the sharpened annular edge;
   ultrasonically vibrating the hollow tube;
   engaging the material with the sharpened annular edge of the vibrating tube for removing the material and reducing said material into smaller particles;

introducing a liquid to the vicinity of the unwanted material to provide irrigation of such material; and generating a core stream of the liquid through the passage in the tube adjacent said tube end to generate a vortex action in the passage by boundary layer effect in the enlargement in the passage to clear the unwanted material, assist in reducing the size of the particles to prevent clogging in said passage and prevent cavitation.

8. The method of claim 7 wherein the passage has a substantially uniform diameter and communicates directly with the enlargement in the passage to provide for a circulation of the particles in a vortex ring in the space beyond and around the end of the tube and an impact of particles against the shaprened annular edge of the tube for a cutting of the particles into particles of reduced size.

9. The method of claim 7 wherein is provided the additional step of roughening the surface inside the enlargement in the passage at the other end of the tube to facilitate the cutting of the particles.

10. Apparatus for removing a cataract from the eye of a patient wherein a saline solution is introduced to the patient's eye comprising:

means for generating energy at an ultrasonic frequency, a probe tip attached to said energy generating means, said tip having an interior passage and a cutting edge, said energy generating means vibrating the tip at the ultrasonic frequency, the interior passage communicating with the cutting edge, the interior passage having a first particular diameter at an end displaced from the cutting edge and an enlargement in a portion of the probe tip at an end adjacent the cutting edge, the enlargement of the passage having a second particular diameter and communicating directly with the interior passage of the first particular diameter and having a sufficient axial length to generate a clearance and a circulating area of particles around the cutting edge of the tip to assure maximum cutting of the particles by the cutting edge, and means for aspirating the saline solution and particles of the cataract from the patient's eye.

11. Apparatus as set forth in claim 10, wherein said enlargement of the passage is of a diameter and axial length relative to the passage of the first particular diameter to emulsify the particles in said passage.

12. Apparatus as set forth in claim 10, wherein the energy-generating means, the probe tip and the aspirating means are in axial alignment.

13. In combination for use in removing a cataract from a patient's eye:

means for providing vibrations at an ultrasonic frequency, a probe tip coupled to the vibrating means for vibration at the ultrasonic frequency and having a cutting edge, a passage, said passage extending through said probe tip and communicating with the cutting edge and having a substantially uniform diameter at the end of the probe tip displaced from the operative end, and and an enlargement in the passage at the operative end of the probe tip adjacent the cutting edge and communicating directly with the passage of substantially uniform diameter to provide a clearance and a circulating area with a vortex action in the enlargement for enhancement of the cutting action and for an emulsifying action on the particles during the vibration of the probe tip at the ultrasonic frequency.

14. In the combination as set forth in claim 13, wherein the enlargement in the passage at the operative end of the probe tip has a diameter and an axial length to facilitate movement of particles against the cutting edge for enhanced cutting action.

15. In the combination set forth in claim 14, wherein the outer diameter of the probe tip is substantially constant.

16. In the combination as set forth in claim 15, wherein the surface defining the enlargement in the passage in the probe tip is roughened.

17. In the combination set forth in claim 13, wherein said enlargement of the passage is defined by an inner wall roughened to facilitate the emulsifying action on the particles.

18. A probe tip for use in removing a cataract from the eye of a patient comprising:

a cylindrical tube adapted to be vibrated by ultrasonic vibration in intra-operative use, a cutting edge provided at one end of the tube, and a passage extending through the tube and communicating with the cutting edge, said passage having a first diameter at the end adjacent the cutting edge and a second diameter at the end removed from the cutting edge, said first diameter being greater than the second diameter, the portion of the passage with the first diameter communicating directly with the portion of the passage with the second diameter whereby, upon an ultrasonic vibration of the tube, a clearance and a circulation area are provided around the cutting edge to facilitate the formation of the removed portions of the cataract into particles.

19. The probe tip as set forth in claim 18, wherein said first passage includes an interior wall having a roughened surface.

20. The probe tip as set forth in claim 19, wherein said probe tip is fabricated from titanium.

21. The probe tip as set forth in claim 18, wherein said cutting edge of the tube is hardened and the outer diameter of the tube is substantially constant.

* * * * *